(12) United States Patent
Shoup

(10) Patent No.: US 7,156,658 B2
(45) Date of Patent: Jan. 2, 2007

(54) DENTAL MEASUREMENT DEVICE

(76) Inventor: Randolph K. Shoup, 8502 N. Carroll Rd., Indianapolis, IN (US) 46236

( * ) Notice: Subject to any disclaimer, the term of this patent is extended or adjusted under 35 U.S.C. 154(b) by 214 days.

(21) Appl. No.: 10/919,644

(22) Filed: Aug. 17, 2004

(65) Prior Publication Data

US 2006/0040232 A1 Feb. 23, 2006

(51) Int. Cl.
*A61C 19/04* (2006.01)
(52) U.S. Cl. .......................... 433/72; 33/514
(58) Field of Classification Search ............ 433/72–75; 33/513–514
See application file for complete search history.

(56) References Cited

U.S. PATENT DOCUMENTS

| 90,705 | A | | 6/1869 | Von Bonhorst | |
|---|---|---|---|---|---|
| 1,649,664 | A | | 11/1927 | Carter | |
| 1,944,801 | A | | 1/1934 | Gulick | |
| 2,758,375 | A | * | 8/1956 | Badovinac et al. | 433/68 |
| 3,106,779 | A | * | 10/1963 | Benjamin | 33/513 |
| 4,286,947 | A | | 9/1981 | Daiberl | |
| RE31,426 | E | | 10/1983 | Daiberl | |
| 4,634,377 | A | * | 1/1987 | Behrend | 433/73 |
| 4,823,476 | A | * | 4/1989 | Curtin | 33/512 |
| 4,843,720 | A | | 7/1989 | Kim | |
| 4,997,368 | A | | 3/1991 | Mayer et al. | |
| 5,685,084 | A | | 11/1997 | Demers | |
| 5,971,756 | A | * | 10/1999 | Fjelstad | 433/68 |
| 6,048,322 | A | | 4/2000 | Kushida | |
| 6,213,959 | B1 | | 4/2001 | Kushida | |
| 2004/0177852 | A1 | * | 9/2004 | Abramson | 128/848 |
| 2006/0040232 | A1 | * | 2/2006 | Shoup | 433/72 |
| 2006/0147872 | A1 | * | 7/2006 | Andreiko | 433/24 |

* cited by examiner

Primary Examiner—Cary E. O'Connor
(74) Attorney, Agent, or Firm—Kyle S. Brant

(57) ABSTRACT

A dental measurement device is disclosed that includes a mouthpiece having a bracket attached thereto and extending outward therefrom. A bite registration compound is applied to the mouthpiece and the mouthpiece is positioned in a patient's oral cavity. The bracket extends outward in front of the patient's face. The bracket includes a vertically oriented planar attachment surface to which measurement devices such as planar rulers are readily attached using adhesives or mechanical fasteners. The rulers include reference markings. The rulers are positioned prior to attachment such that the reference markings align with the anterior midline and incisal edge locations of the patient. Such reference positions are then available for later use in fabricating dental restorations. Alternatively, anterior midline and incisal edge locations are identified by application of permanent markings to the rulers.

17 Claims, 3 Drawing Sheets

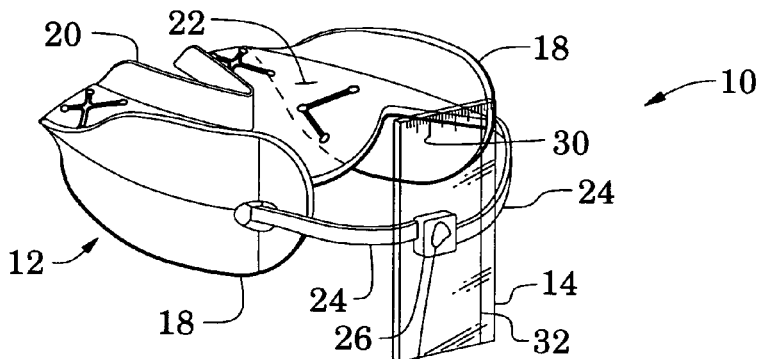
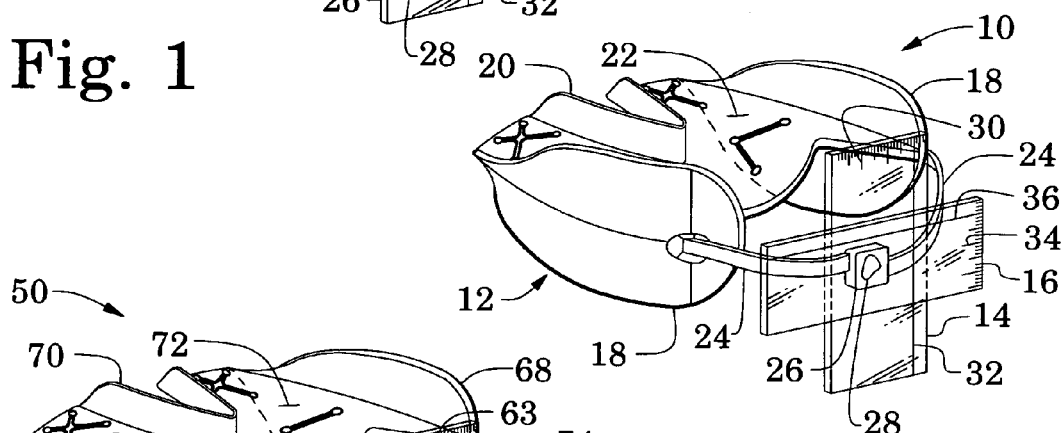
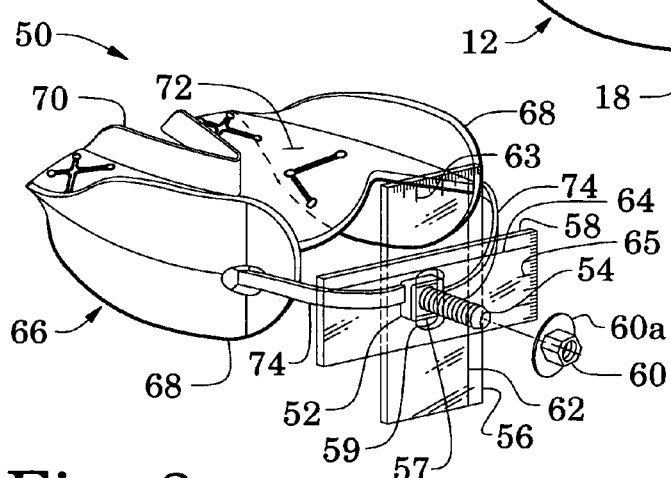
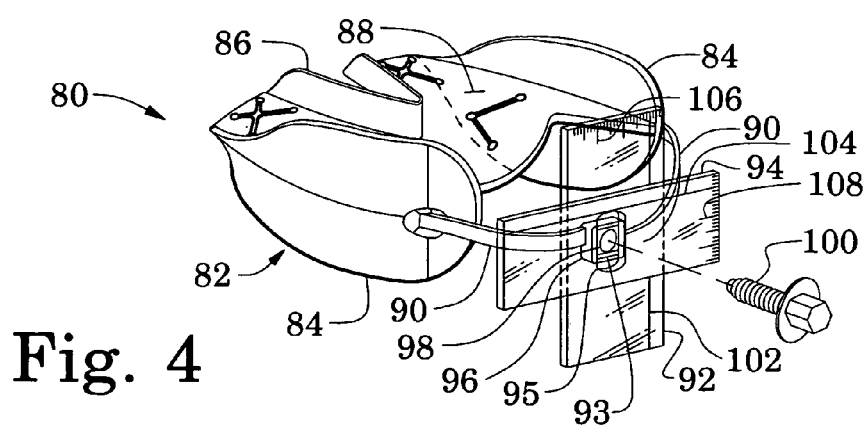
Fig. 1
Fig. 2
Fig. 3
Fig. 4

1

DENTAL MEASUREMENT DEVICE

FIELD OF THE INVENTION

This invention relates in general to dental measurement devices, and more specifically, to devices useful in accurately determining anterior midline and incisal edge position of the patient.

BACKGROUND OF THE INVENTION

Fabrication of upper and lower anterior dental restorations requires careful measurement of numerous dimensions of the patients physical jaw and oral cavity in order to construct upper and lower restorations so that their relative positions in the patient's oral cavity restore a natural occlusion. The known techniques typically include establishing specific reference locations relative to the positions of the teeth in the upper and lower jaws. These reference locations establish exact positions of patterns for replacing natural teeth with anterior dental restorations.

Many of the devices of the prior art are overly complex, expensive, and/or cumbersome to use. A further shortcoming of the prior art is the lack of a reliable yet simple mechanism for ascertaining the anterior midline and incisal edge position of the patient with respect to the patient's bite registration. Such measurement information can be used by a lab technician to precisely align the anterior restorations to the exact specifications of the dentist. A measuring device useful in obtaining such dimensions that is disposable yet inexpensive so that the cost thereof is readily borne by each patient would serve to enhance the ability to establish a permanent record of such critical dimensions useful in fabricating dental restorations. Further, a device that is capable of obtaining midline and incisal edge position measurements relative to bite registration is needed. Such measurement data along with the patient's models and impressions can be used by a lab technician to precisely align the anterior restorations to the exact specifications of the dentist.

SUMMARY OF THE INVENTION

A dental measurement device, according to one aspect of the present invention, for determining reference dimensions for dental restorations, is comprised of an oral registration device including a semi-elliptical planar member that is horizontally oriented and generally conforms with the bite opening in the patients oral cavity and is insertable therein, the oral registration device further including vertical walls extending upward and downward and situated along the outer edges of the semi-elliptical planar member, a protrusion extending outward from the semi-elliptical member such that the protrusion extends outward from within the patient's mouth when the oral registration device is disposed in the patient's mouth, a midline measurement device attached to the protrusion in a position to dimensionally establish the patient's facial midline, and an incisal edge measurement device attached to the protrusion in a position to dimensionally establish the patient's incisal edge position.

One object of the present invention is to provide an improved dental measurement device for use in dental restoration fabrication.

Another object of the present invention is to provide an inexpensive disposable dental measurement device suitable for taking a bite impression and establishing anterior midline and incisal edge location information.

Still another object of the present invention is to provide an improved mechanism for determining and providing spatial measurement information to dental restoration fabricators.

These and other objects of the present invention will become more apparent from the following description of the preferred embodiments.

BRIEF DESCRIPTION OF THE DRAWINGS

FIG. 1 is a perspective view of a dental measurement device according to one aspect of the present invention.

FIG. 2 is a perspective view of the dental measurement device of FIG. 1 depicting two measurement rulers attached thereto.

FIG. 3 is a perspective view of a dental measurement device according to a second aspect of the present invention.

FIG. 4 is a perspective view of a dental measurement device according to a third aspect of the present invention.

DESCRIPTION OF THE PREFERRED EMBODIMENT

Figure 5:
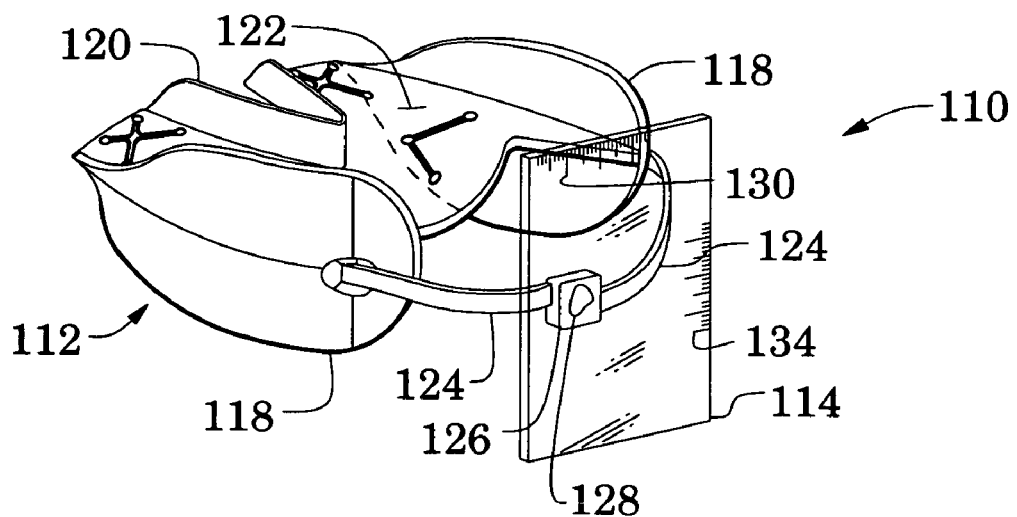
FIG. 5 is a perspective view of a dental measurement device according to a fourth aspect of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Referring now to FIGS. 1 and 2, a dental measurement device 10 according to one aspect of the present invention is shown. Dental measurement device 10 is comprised of a mouthpiece 12, ruler 14 and ruler 16. Mouthpiece 12 includes side walls 18, inner wall 20, a semi-elliptical bite plate 22, support bracket 24 and mounting plate 26. Side walls 18 extend upward and downward from the outer edges of bite plate 22. Inner wall 20 extends upward and downward from a central portion of bite plate 22 to a height less than that of side walls 18. Support bracket 24 includes an integrally formed mounting plate 26 that is a substantially vertically oriented planar surface. Mounting plate 26 is horizontally and vertically offset from the horizontal center line of bite plate 22. Mouthpiece 12 is preferably a plastic molded integral assembly though the component parts thereof (side walls 18, inner wall 20, bite plate 22 and support bracket 24) may be constructed separately and bonded together using techniques well known in the art such as ultrasonic welding, mechanical attachment mechanisms (such as slots and tabs with locking mechanisms) or adhesives.

Operationally speaking, mouthpiece 12 is designed and sized for placement within a patient's oral cavity. A bite registration material or impression compound (not shown) is applied to the upper and lower surfaces of bite plate 22 between the side walls 18 and inner wall 20. Such compounds are well known in the dental arts. Once the impression compound is applied, mouthpiece 12 is situated within the patient's oral cavity and the patient bites on the bite plate 22 to secure the mouthpiece in position and forming a dental impression in the compound. Once the mouthpiece 12 is fixed in position within the oral cavity and the compound has cured, a small amount of adhesive is applied to mounting plate 26 at location 28. A fast setting adhesive such as cyanoacrylate based adhesives well known for their strength and rapid curing time is a preferred adhesive for use with the dental measurement devices of the present invention. Ruler 14 (preferably constructed from clear plastic material) is next positioned vertically in contact with mounting plate 26, as shown in FIG. 1. Ruler 14 includes an array of measurement markings 30 along the upper edge thereof as well as an alignment mark 32 that extends linearly along the surface of ruler 14. Ruler 14 is positioned such that alignment mark 32 is aligned with the patient's anterior midline or median line, an imaginary line that bisects the dental arch at the center thereof. Once the fast setting adhesive secures ruler 14 to mounting plate 26, another small amount of adhesive is applied to ruler 14 as noted at 28 and ruler 16 is positioned adjacent ruler 14 in a ninety degree rotated location as shown in FIG. 2 in contact with ruler 14. Ruler 16 is quickly moved so that alignment mark 36 is aligned in horizontal alignment with the incisal edge position of the patient. Ruler 16 is maintained in this position until the adhesive cures. Once rulers 14 and 16 are correctly positioned and permanently attached to mouthpiece 12, the patients measurement information derived from the anterior midline and incisal edge locations with respect to the bite impression is used by a lab technician to precisely align and construct dental restorations to the exact specifications of the dentist.

An alternative approach to use and implementation of dental device 10 is as follows. Bite registration compound is applied to bite plate 22 and inserted in the patient's oral cavity. Once the patient bites down on the bite plate and the compound has cured, rulers 14 and 16 are attached to mounting plate 26 and a permanent ink marking pen is used to apply a mark along the upper edge of ruler 14 to identify the exact location of the anterior midline. Next, the incisal edge position is recorded by applying a permanent ink marking to the vertical edge of ruler 16. Once the ink markings are applied, a lab technician has reference locations for the anterior midline and incisal edge with respect to the bite impression that are useful in the fabrication of dental restorations. A sharp tool may be used to scribe a mark into the surface of rulers 14 and 16 as an alternative to the use of permanent ink marking described above.

Referring now to FIG. 3, another embodiment of a dental measurement device 50 according to the present invention is shown. Device 50 includes substantially the same components as device 10 with the exception of the configuration of the mounting plate and rulers. Specifically, mounting plate 52 includes a threaded stud 54 attached thereto and extending horizontally outward from mounting plate 52. Rulers 56 and 58 include slotted aperture 57 and 59, respectively. Preferably, stud 54 is integrally formed with mounting plate 52 by use of injection molding techniques. Mounting nut 60 includes an integral washer 60a. Nut 60 is threaded onto mounting stud 54 to secure rulers 56 and 58 in position. Ruler 56 is positioned so that alignment mark 62 is aligned with the anterior midline of the face. Ruler 58 is positioned so that alignment mark 64 is aligned with the incisal edge of the patient's mouth. Nut 60 is then tightened to secure rulers 56 and 58 in position. It is also contemplated that application of a small amount of adhesive to the edges of the mounting plate 52 adjacent ruler 56 and in the physically adjacent interface between rulers 56 and 58 will serve to permanently secure mouthpiece 66 and rulers 56 and 58 in spatially fixed position with respect to one another. Alternatively, a dental practitioner may use a permanent marking device, such as a permanent ink pen or a sharp instrument, to record the patient's anterior midline location along tick marks 63 and the patient's incisal edge position along tick marks 65.

Also shown in FIG. 3 are mouthpiece 66, side walls 68, inner wall 70, bite plate 72, and support bracket 74 which are identical in form and function to the correspondingly identified items shown in FIG. 1. Rulers 56 and 58 and mounting plate 52 comprise those components of device 50 having features different from those of device 10.

Figure 7:
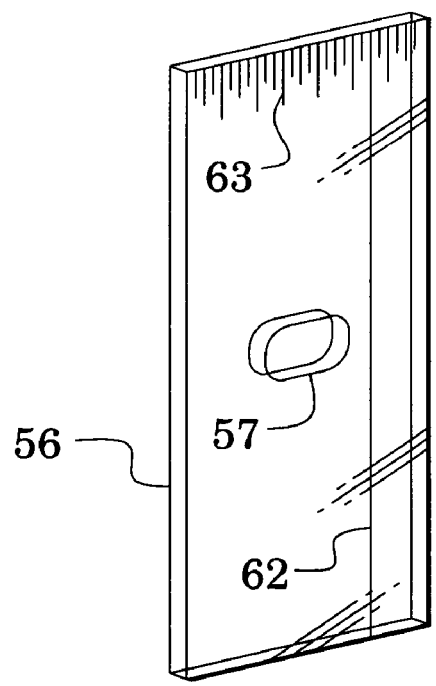
FIG. 7 is a perspective view of rulers 56 and 58 of FIG. 3 and rulers 92 and 94 of FIG. 4.
Figure 8:
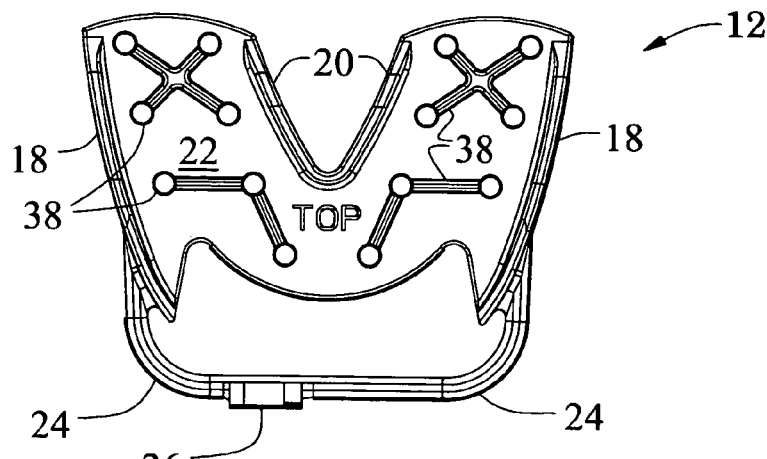
FIG. 8 is a plan view of mouthpiece 12 of FIGS. 1 and 2.
Figure 9:
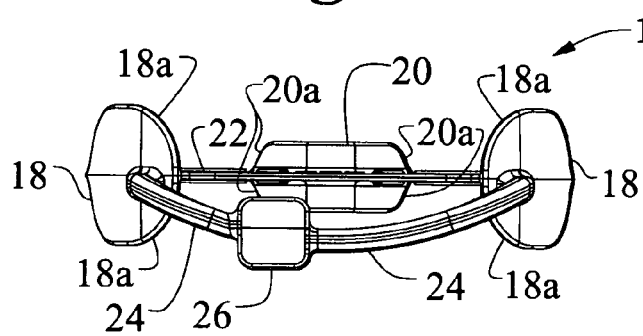
FIG. 9 is a front elevational view of mouthpiece 12 of FIGS. 1 and 2.
Figure 10:
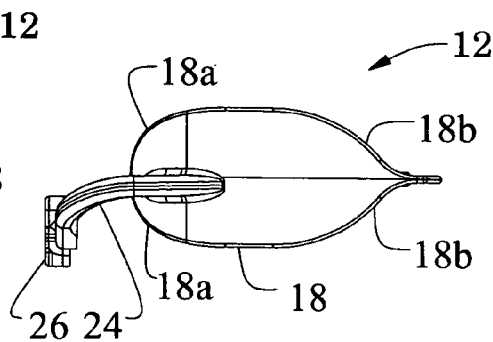
FIG. 10 is a side elevational view of mouthpiece 12 of FIGS. 1 and 2.
Figure 11:
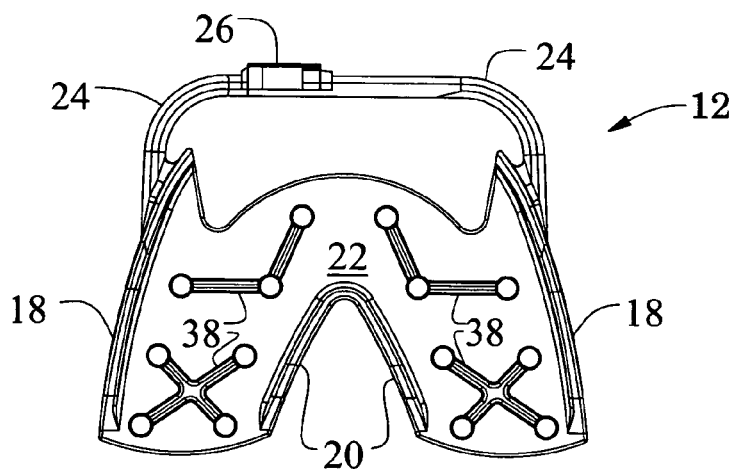
FIG. 11 is a bottom view of mouthpiece 12 of FIGS. 1 and 2.

Referring now to FIG. 4, another embodiment of a dental measurement device 80 according to the present invention is shown. Device 80 includes mouthpiece 82, rulers 92 and 94 and bolt 100. Those items identical with similarly identified items in FIGS. 1 and 3 include side walls 84, inner wall 86, bite plate 88 and support bracket 90. Rulers 92 and 94 include slotted apertures 93 and 95, respectively (apertures 93 and 95 are depicted in FIG. 7). Mounting plate 96 is suspended in position by support bracket 90. Mounting plate 96 includes a threaded aperture 98 that receives bolt 100 therein. In practice, rulers 92 and 94 are positioned over threaded aperture 98 so that bolt 100 is insertable through slotted apertures 93 and 95. Bolt 100 is tightened so that rulers 92 and 94 are held in position yet movable so that ruler 90 is movable horizontally and alignment marking 102 can be situated in alignment with the patient's anterior midline. Similarly, ruler 92 is movable in a generally vertical direction so that alignment marking 104 is situated in alignment with the patient's incisal edge location. Alternatively, rulers 92 and 94 can be positioned substantially as shown and the anterior midline and incisal edge locations are recorded by using a permanent marking device to apply markings along the measurement tick marks 106 and 108, respectively. As previously suggested, the use of an adhesive is optional to secure rulers 92 and 94 to one another and to mounting plate 96.

Referring now to FIG. 5, a dental measurement device 110 according to yet another aspect of the present invention is shown. Dental device 110 is comprised of mouthpiece 112 and ruler 114. Mouthpiece 112 includes side walls 118, inner wall 120, bite plate 122, support bracket 124 and mounting plate 126. Side walls 118 extend upward and downward from bite plate 122. Inner wall 120 extends upward and downward from bite plate 122 to a height less than that of side walls 118. Support bracket 124 includes an integrally formed mounting plate 126 that is a substantially vertically oriented planar surface. Mounting plate 126 is horizontally and vertically offset from the horizontal center line of bite plate 122. Mouthpiece 112 is preferably a plastic molded integral assembly though the component parts thereof (side walls 118, inner wall 120, bite plate 122 and support bracket 124) may be constructed separately and bonded together using techniques well known in the art such as ultrasonic welding, mechanical attachment mechanisms (such as slots and tabs with locking mechanisms) or adhesives. Mouthpiece 112 is identical to mouthpiece 12 of FIGS. 1 and 2. Ruler 114 is larger in the horizontal dimension when compared with Ruler 14. Ruler 114 is attached to bite plate 126 using adhesive at 128, though the attachment mechanisms of FIGS. 3 and 4 are also contemplated as suitable substitute attachment approaches to attach measurement ruler 114 to mouthpiece 112.

Figure 6:
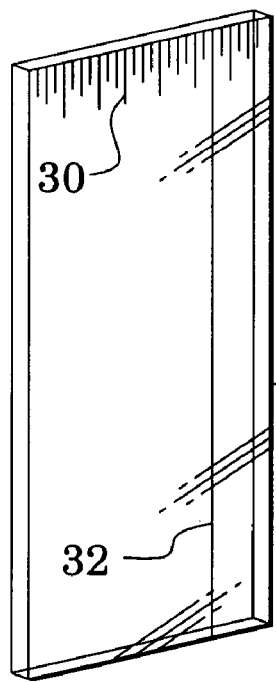
FIG. 6 is a perspective view of rulers 14 and 16 shown in FIG. 2.

Use of device 110 includes applying a bite registration material or impression compound to the upper and lower surfaces of bite plate between side walls 118 and inner wall 120. Next, mouthpiece 112 is situated in a patient's oral cavity and the patient is instructed to bite down on bite plate 122 until the compound cures. Once the bite registration material has cured or solidified, a dentist records the position of the patient's anterior midline by applying a permanent mark along tick marks 130. Next, the dental practitioner records the position of the patient's incisal edge by applying a permanent mark along tick marks 134. Once the anterior midline and incisal edge locations are recorded, dental measurement device 110 is used by a lab technician to precisely align and construct dental restorations to the exact specifications of the dentist Referring now to FIG. 6, a perspective view of ruler 14 of FIGS. 1 and 2 is shown. Ruler 14 is, for convenience, a transparent plastic ruler including alignment marking 32 and measurement marks or tick marks 30. Since ruler 14 is constructed from clear plastic, is should be readily apparent how ruler 14 can be repositioned to provide the features and functionality of ruler 16 as shown in FIGS. 1 and 2.

Referring now to FIG. 7, ruler 56 of FIG. 3 is shown. Ruler 56 includes measurement marks or tick marks 63 and an alignment mark 62. A slotted aperture 57 is shown that enables adjustment of ruler 56 along a line perpendicular to alignment mark 62. Ruler 92 is identical with ruler 56. Rulers 58 and 92 are physically and functionally identical to ruler 56 except for being repositioned to achieve desired positioning of the alignment marks and tick marks.

Referring now to FIGS. 8–11, a plan view, front elevational view, side elevational view and bottom view of mouthpiece 12 are shown. Mouthpiece 12 includes side walls 18 extending upward and downward from bite plate 22. Side walls 18 include a rounded leading edge 18a and a tapered trailing edge 18b where the height of side walls 18 tapers down to the thickness of bite plate 22 to reduce patient discomfort. Inner wall 20 extends upward and downward from the inner area of bite plate 22 and includes rounded edges 20a to eliminate patient discomfort upon insertion of mouthpiece 12 into a patient's oral cavity. Support bracket 24 is attached to and extends outward from side walls 18 as shown. Mounting plate 26 is attached to support bracket 24 and is offset from the center of bite plate 22 and disposed slightly below bite plate 22. Offsetting the position of mounting plate 26 from the center of bite plate 22 enables the practitioner to more easily identify the anterior midline and incisal edge locations of the patient. Support ribs 38 provide added structural integrity to bite plate 22. Mouthpiece 12 is preferably constructed using an injection molding process to produce a single unitary assembly as shown. Materials for fabrication of mouthpiece 12 include any of various plastic, rigid rubber or synthetic rigid rubber compounds well known in the art. It is also contemplated that certain portions of mouthpiece 12 may be fabricated separately and attached to one another to create the assembly shown. Adhesives or ultrasonic welding techniques are well known to fabricate mouthpiece 12 from component parts and attach such parts into a unitary assembly.

It should be readily apparent how the mouthpiece 12 of FIGS. 8–11 is modified to arrive at the configuration of the mouthpieces shown in FIGS. 3 and 4 by altering the configuration of mounting plate 26 to include a threaded stud (FIG. 3) or a threaded aperture (FIG. 4). In all other respects, the mouthpieces 66 and 82 are identical to mouthpiece 12.

All of the embodiments of the dental measurement devices disclosed herein are contemplated as being constructed of plastic or other suitable material wherein the mounting plates are fixed in position with respect to the bite plates. The rulers are preferably constructed of transparent plastic, though translucent or opaque plastic may also be used. The spatial relationship between the bite registration obtained using the bite registration material and the markings on the rulers establishing the anterior midline and the incisal edge with respect to the bite registration are essential in properly constructing dental restorations of a desired design.

It is also contemplated that any of various mechanical clamping mechanisms known in the art, including but not limited to a spring clip, a c-clamp or the like, may be used to attach ruler 14 and 16 to mounting plate 26 of FIGS. 1 and 2 in place of the use of adhesives.

While the invention has been illustrated and described in detail in the drawings and foregoing description of the preferred embodiments, the same is to be considered as illustrative and not restrictive in character, it being understood that only the preferred embodiments have been shown and described and that all changes and modifications that come within the spirit of the invention are desired to be protected.

What is claimed is:

1. A method of determining a patient's facial midline and incisal edge position with respect to the patient's bite registration for use in fabricating dental restorations, said method comprising the steps of:
   providing a dental measurement device consisting of:
      a) an oral registration device including a semi-elliptical planar member that is horizontally oriented and inserted into the patients oral cavity, said oral registration device further including thin vertical walls extending upward and downward from the outer elliptical edges of said semi-elliptical planar member;
      b) a protrusion extending outward from said semi-elliptical member;
      c) a midline measurement device;
      d) an incisal edge measurement device;
   applying a bite registration material to the surfaces of said oral registration device;
   positioning said dental measurement device in a patients oral cavity to establish a bite registration;
   attaching said midline measurement device to said protrusion such that the patient's facial midline is spatially identified with respect to said bite registration by the position of said midline measurement device; and
   attaching said incisal edge measurement device to said protrusion such that the patient's incisal edge is spatially identified with respect to said bite registration by the position of said incisal edge measurement device.

2. The method of claim 1 wherein said midline measurement device includes a midline alignment marking and said incisal edge measurement device includes an incisal alignment marking and wherein said attaching said midline measurement device includes the step of aligning said midline alignment marking with the patients anterior midline and wherein said attaching said incisal measurement device includes the step of aligning said incisal alignment marking with the patient's incisal edge position.

3. The method of claim 2 wherein said midline measurement device and said incisal edge measurement device are removably attached to said protrusion.

4. The method of claim 2 wherein said midline measurement device and said incisal edge measurement device are permanently attached to said protrusion using an adhesive.

5. The method of claim 2 wherein said dental measurement device is constructed of plastic material and said midline measurement device and said incisal measurement device are both constructed of a transparent plastic material.

6. A dental measurement device for determining reference dimensions for dental restorations, the device comprising:
an oral registration device including a semi-elliptical planar member that is horizontally oriented and generally conforms with the bite opening in the patients oral cavity and is insertable therein, said oral registration device further including thin vertical walls extending upward and downward from the outer elliptical edges of said semi-elliptical planar member;
a protrusion extending outward from said semi-elliptical member such that said protrusion extends outward from within the patient's mouth when said oral registration device is disposed in the patient's mouth;
a midline measurement device attached to said protrusion and oriented in a position to dimensionally establish the patient's facial midline; and
an incisal edge measurement device attached to said protrusion and oriented in a position to dimensionally establish the patient's incisal edge position.

7. The device of claim 6 wherein said midline measurement device and said incisal edge measurement device are removably attached to said protrusion.

8. The device of claim 6 wherein said protrusion includes a substantially vertical planar surface at the distal end thereof and said midline measurement device and said incisal edge measurement device are attached to said vertical planar surface.

9. The device of claim 8 wherein said midline measurement device and said incisal edge measurement device are removably attached to said vertical planar surface.

10. The device of claim 8 wherein said midline measurement device and said incisal edge measurement device are constructed of transparent materials so that the patent's face is viewable therethrough.

11. The device of claim 10 including attachment means disposed on said substantially vertical planar surface for attaching said midline measurement device and said incisal edge measurement device thereto, and wherein said midline measurement device includes a slotted aperture therein for engaging a portion of said attachment means, and wherein said incisal edge measurement device includes a slotted aperture therein for engaging a portion of said attachment means.

12. The device of claim 11 wherein said attachment means includes a threaded stud extending perpendicularly outward from said substantially vertical surface and a threaded nut sized to engage said threaded stud.

13. A dental measurement device comprising:
an oral registration device including a semi-elliptical planar member that is horizontally oriented and conforms to the size of the bite opening in the patients oral cavity and is insertable therein, said oral registration device further including thin substantially vertical walls extending upward and downward from the outer elliptical edges of said semi-elliptical planar member;
a bracket attached to and extending substantially horizontally outward from said semi-elliptical member such that said bracket extends outward from within the patient's mouth when said oral registration device is disposed in the patient's mouth;
a mounting plate attached to said bracket and consisting of a substantially planar vertically oriented surface;
a measurement device having a thin planar rectangular configuration and attached to said mounting plate and oriented in a position to establish the patient's facial midline location and incisal edge location.

14. The device of claim 13 wherein said measurement device is removably attached to said mounting plate.

15. The device of claim 14 wherein said measurement device includes a thin planar rectangular midline measurement device and a thin planar rectangular incisal edge measurement device and wherein said midline measurement device includes a midline alignment marking and said incisal edge measurement device includes an incisal alignment marking and wherein said midline alignment marking is aligned with the patient's anterior midline location and said incisal alignment marking is aligned with the patient's incisal edge location.

16. The device of claim 15 wherein said mounting plate includes a threaded stud extending perpendicularly outward therefrom and wherein said midline measurement device and said incisal edge measurement device both include a slotted aperture therein to receive said threaded stud, the dental measurement device further including a nut that mates with said threaded stud to secure said midline and incisal edge measurement devices to said mounting plate.

17. The device of claim 15 wherein said mounting plate includes a threaded aperture and wherein said midline measurement device and said incisal edge measurement device both include a slotted aperture therein, and wherein the dental measurement device further includes a bolt having threads that mate with said threaded aperture and said bolt being inserted through said slotted apertures in said midline and incisal edge measurement devices and into said threaded aperture to secure said midline and incisal edge measurement devices to said mounting plate.

* * * * *